(12) United States Patent
Kunjachan

(10) Patent No.: US 8,716,363 B2
(45) Date of Patent: May 6, 2014

(54) BIODEGRADABLE PUTTY COMPOSITIONS AND IMPLANT DEVICES, METHODS, AND KITS RELATING TO THE SAME

(75) Inventor: Vipin Kunjachan, Audubon, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 13/246,999

(22) Filed: Sep. 28, 2011

(65) Prior Publication Data

US 2013/0078312 A1     Mar. 28, 2013

(51) Int. Cl.
*A61F 2/02*       (2006.01)
*A61K 31/66*      (2006.01)
*A61K 31/685*     (2006.01)

(52) U.S. Cl.
USPC .............. 523/115; 523/113; 514/75; 514/76; 514/109

(58) Field of Classification Search
USPC ................ 523/115, 113; 514/75, 76, 109
See application file for complete search history.

(56) References Cited

U.S. PATENT DOCUMENTS

2004/0202640 A1* 10/2004 Crandall ................... 424/78.26
2009/0068255 A1*  3/2009 Yu et al. ........................ 424/450

\* cited by examiner

*Primary Examiner* — Michael Pepitone

(57) ABSTRACT

Disclosed are phospholipid based compositions and implant devices, as well as methods and kits that include such compositions or components thereof. In particular, the present compositions include a polymer component such as a poloxamer or PEG component and a phospholipid component, such as a Phosal. The present compositions may include at least one additional component, such as granules, powder and/or particulates. The present compositions may further include one or more bone graft materials and/or active ingredients. The compositions may be used on their own or incorporated on or in a surgical implant.

13 Claims, 6 Drawing Sheets

*MicroFuse Granules*

*MicroFuse Granules*

*Bioresorbable carrier*

*MicroFuse Granules*     *Bioresorbable carrier*

*MicroFuse Putty*

BIODEGRADABLE PUTTY COMPOSITIONS AND IMPLANT DEVICES, METHODS, AND KITS RELATING TO THE SAME

FIELD

The present invention generally relates to carrier compositions which may be used to carry e.g., bone graft materials and/or for drug delivery to a mammal. Example carrier compositions include phospholipid-based carriers that may be prepared e.g., in the form of a putty or paste. The invention also generally relates to implant devices and methods of making and using the present compositions, as well as kits that include such compositions or components thereof.

BACKGROUND

First generation synthetic bone graft substitutes were in the form of loose particles, beads, etc. Examples includes Vitoss bone void filler, ActiFuse granules etc. The intraoperative handling of these products has presented a challenge during surgery, however.

SUMMARY

The present inventor has developed novel phospholipid-based carriers which may be useful, e.g., to carry and improve the handling characteristics of granules, such as MicroFuse® Granules (Globus Medical, Inc.), or for carrying powders or particulates. Example phospholipid-based carrier compositions include at least one a polymer component (such as Pluronic/Poloxamer or Polyethylene Glycol (PEG), e.g., Pluronic F127 also known as Poloxamer 407) and at least one soybean derived lipid/phospholipid component (such as Phosal 50PG).

Thus, example embodiments herein are generally related to compositions that include a phospholipid-based carrier that includes at least one polymer (e.g. poloxamer or PEG) component and at least one phospholipid (e.g., Phosal) component. According to non-limiting example embodiments, the present compositions may further include granules, powder and/or particulates. According to non-limiting example embodiments, the present compositions may be in the form of a putty or paste. Alternatively, the carrier may be in the form of a dough-like carrier or have a paste-like consistency, which forms may become more putty-like or flowable when combined with granules, powder and/or particulates. Example embodiments of compositions herein may further include one or more graft materials (such as synthetic BGS) and/or one or more active ingredients.

Other example embodiments include, one or more implant devices that may include a device for placement into a mammal, such as a human, and one or more of the present compositions thereon or therein. The compositions in these embodiments may additionally include any component known to those skilled in the art that may be desirable for implantation with the device, such as one or more bone graft materials and/or active ingredients.

Further provided are methods of making compositions for implantation into a mammal. In the present methods, one may start out with granules (e.g., MicroFuse Granules), powder or particulates; or with a phospholipid-based carrier composition (e.g., MicroFuse Putty) that may contain one or more of granules, powder and particulates; and add blood or bone marrow aspirate (BMA) thereto. The methods may further include mixing the present compositions with at least one component selected from the group consisting of one or more graft materials and one or more active ingredients.

Also provided are methods of treating mammals by administering to a mammal at least one of the present compositions. Such methods may further include administering one or more graft materials and/or one or more active ingredients, either as part of the present compositions or along therewith.

According to non-limiting example embodiments, the present compositions may be administered directly to a mammal, or alternatively in or on an implant that is inserted into a mammal, e.g., during a surgical procedure.

Other example embodiments are directed to kits that include the present compositions or one or more ingredients thereof (such as a polymer and a phospholipid component), and may further include e.g., instructions for making and/or using the compositions; one or more implant devices into or onto which the composition may be incorporated; tools or devices for mixing and/or storing the compositions; tools or devices for inserting the present compositions or implant devices into a mammal; one or more granules, powder or particulates to be added to the composition; one or more graft materials and/or active ingredients that may be provided with or carried by the present compositions; and/or any other components or devices that may be useful in making and/or using the present compositions or implant devices.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF THE FIGURES

Non-limiting example embodiments described herein, with reference to the following accompanying Figures.

Figure 3:
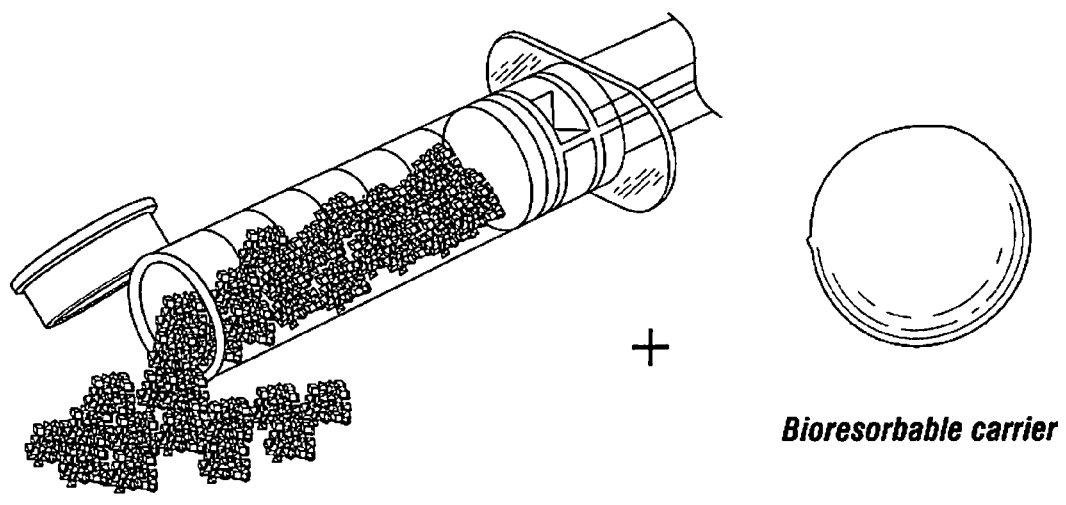
FIG. 3 depicts a non-limiting example of a composition of the present invention, which includes e.g., biodegradable polymer granules, such as the MicroFuse® Granules depicted in FIG. 1, which have been combined with a bioresorbable phospholipid-based carrier, which includes Pluronic F127 and Phosal 50 PG, as depicted in FIG. 2, to form novel compositions according to example embodiments of the present invention.
Figure 3:
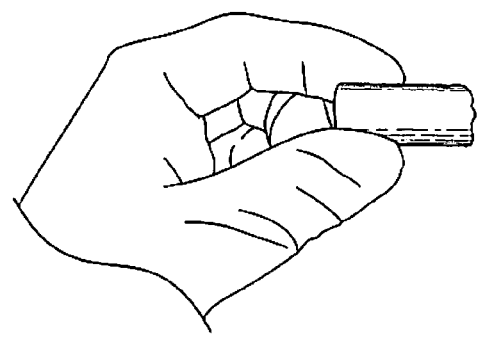
Figure 4:
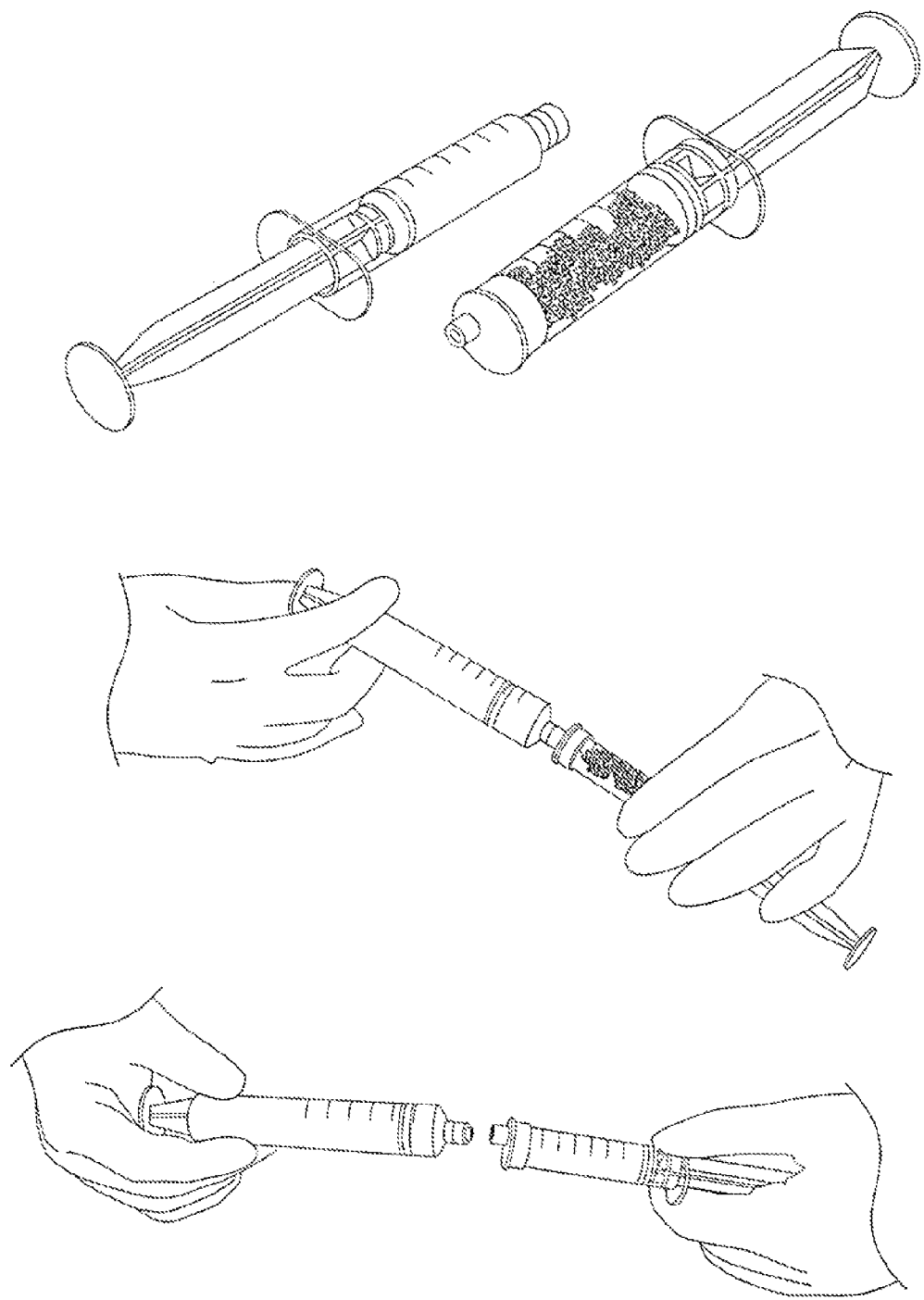
Figure 5:
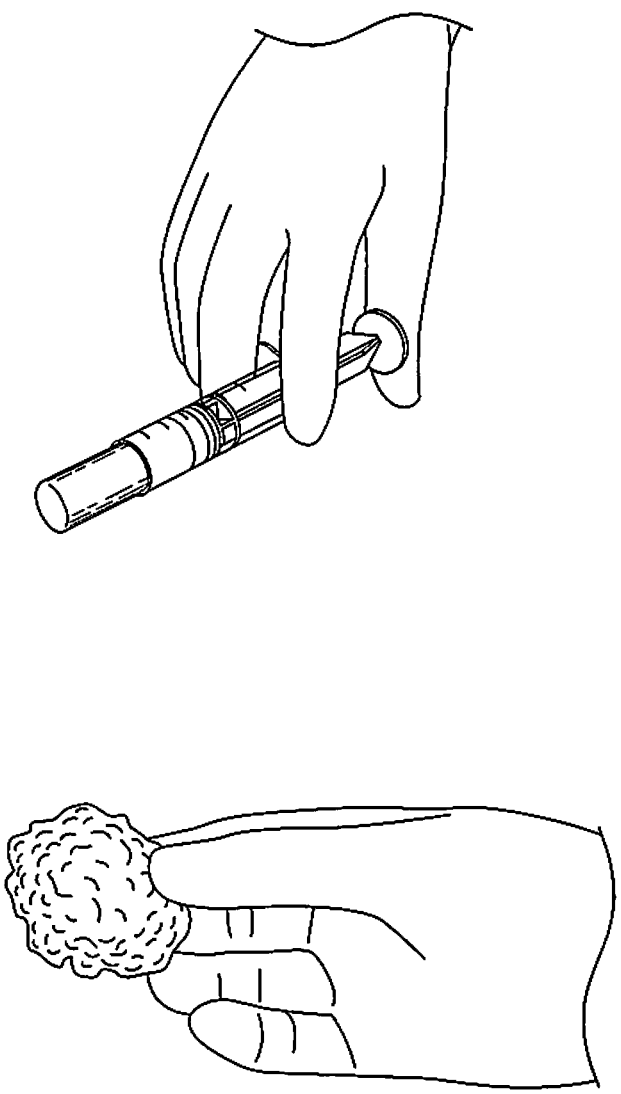
Figure 6:
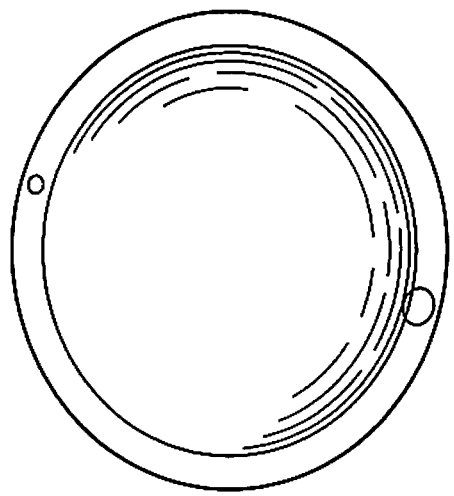
Figure 6:
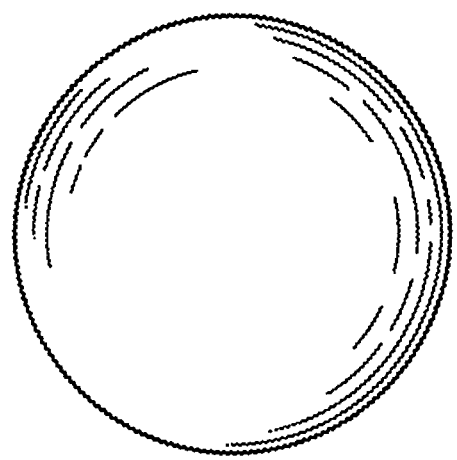
Figure 7:
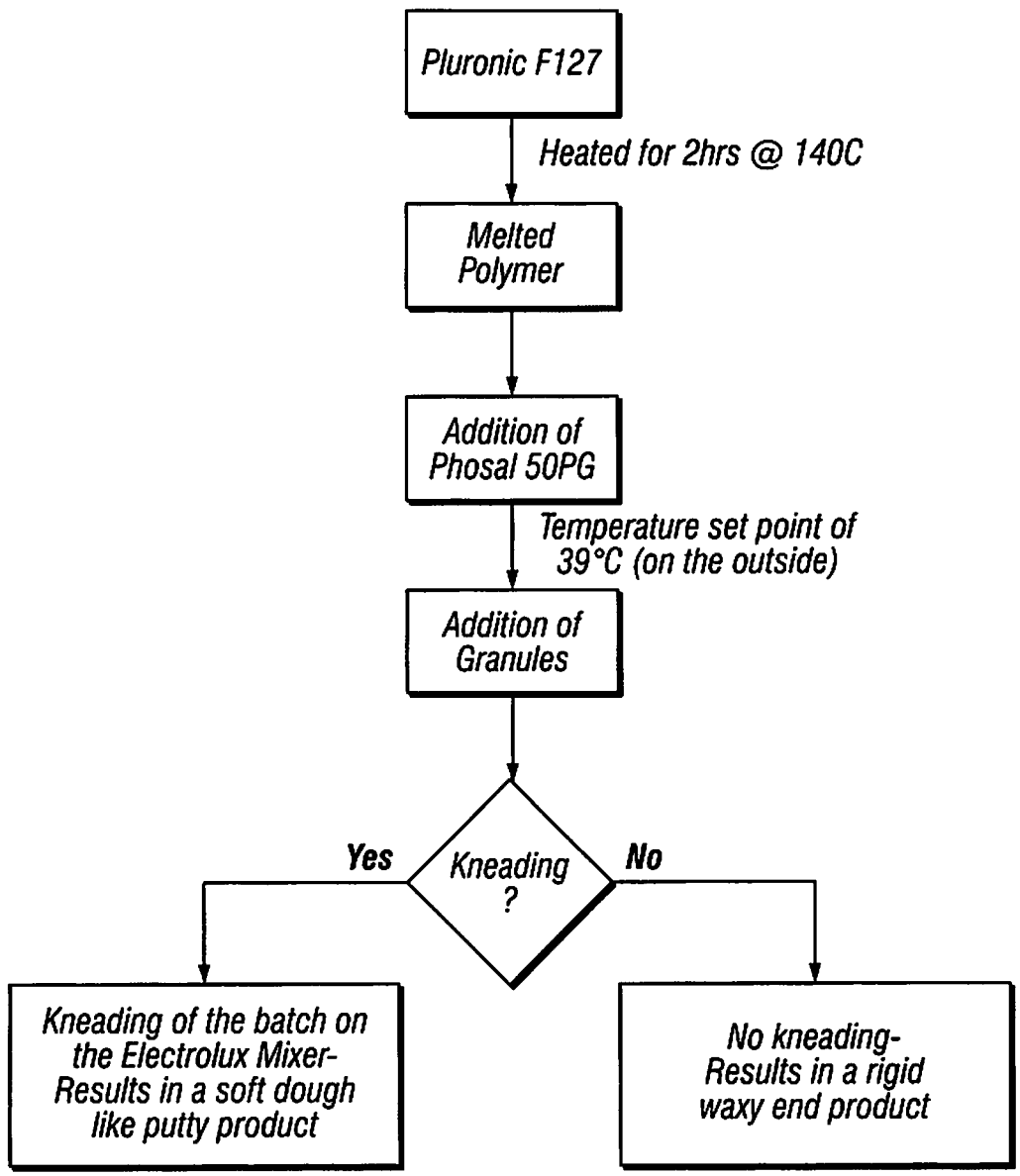

FIG. 4 depicts a method of combining bone marrow aspirate (BMA) with granules, such as MicroFuse® Granules, e.g., using a luer lock syringe;

FIG. 5 depicts a composition according to the present invention, such as the composition depicted in FIG. 3, before (on the left) and after (on the right) being mixed with BMA;

FIG. 6 depicts Pluronic F127 and Phosal 50 PG, which are non-limiting examples of polymers and phospholipids that may be used in accordance with the present invention; and FIG. 7 is a flow chart setting forth an example method of preparing a composition according to the present invention.

DETAILED DESCRIPTION

The aspects, advantages and/or other features of example embodiments of the invention will become apparent in view of the following detailed description, taken in conjunction with the accompanying drawings. In describing example embodiments, specific terminology is employed for the sake of clarity. However, the embodiments are not intended to be limited to this specific terminology. It should be apparent to those skilled in the art that the described embodiments of the present invention provided herein are merely exemplary and illustrative and not limiting. Numerous embodiments of modifications thereof are contemplated as falling within the scope of the present invention and equivalents thereto. It is to be understood that each specific element includes all technical equivalents that operate in a similar manner to accomplish a similar purpose.

Unless otherwise noted, technical terms are used according to conventional usage. Any patents and/or publications mentioned in this specification are indicative of the level of those skilled in the art to which the invention pertains. All publications, patent applications, patents, and other references mentioned herein are incorporated by reference in their entirety.

Amounts and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

As used herein, "a" or "an" may mean one or more. As used herein, "another" may mean at least a second or more. Furthermore, unless otherwise required by context, singular terms include pluralities and plural terms include the singular.

The terms "drug" and "active ingredient" are used herein to include any drug or other active ingredient that may be added to the present compositions for treating mammals, such as humans, for a variety of different conditions.

The terms "granule", "particle," "particulate," "sphere," and "microsphere" are used somewhat interchangeably herein and are intended to encompass granules that are essentially discrete from one another. The term "granule" may include e.g., multiple "spheres", "microspheres" or other particles that may be bonded together, for example, by heating to obtain granules. The terms may include various particles, granules, chips, beads, etc., regardless of shape. Accordingly, the terms "granule", "particle," "particulate," "sphere" and "microsphere" and the like are intended to be very broad and encompass many shapes, including spheres, spheroids, rods, pellets, granules, blocks, grains or any other suitable shape.

A "resorbable" or "biodegradable" material may include for example ceramics, polymers or other materials that are designed to be resorbed by the body of a mammal, and eventually replaced with healthy tissue. The terms "degradation rate," "degradation profile," "resorption rate," and "resorption profile" are all used somewhat interchangeably herein and are intended to refer to the time over which a resorbable material is resorbed by the body. Degradation or resorption rates may vary somewhat depending on various factors such as material selection, placement location in the body, temperature, surrounding tissue, etc.

As used herein, "biocompatible" means the ability of an object to be accepted by and to function in a mammal without eliciting a significant foreign body response (such as, for example, an immune, inflammatory, thrombogenic, or like response).

As used herein, "polymer" means a chemical compound or mixture of compounds formed by polymerization and including repeating structural units. Polymers may be constructed in multiple forms and compositions or combinations of compositions. The term "polymer" is also intended to cover copolymer materials and polymer blends formed from two or more polymers. Examples of suitable polymers that may be used include, but are not limited to, biocompatible and/or bioabsorbable polymers or copolymers and combinations thereof. Non-limiting examples include, poly(hydroxy acids), poly (phosphazenes), poly(amino acid-carbonates), poly(anhydrides), and poly(urethanes).

One of ordinary skill in the art will appreciate that the selection of a suitable polymer depends on several factors. For example, factors in the selection of the appropriate polymer(s) that is used may include bioabsorption (or bio-degradation) kinetics; in vivo mechanical performance; cell response to the material in terms of cell attachment, proliferation, migration and differentiation; and biocompatibility. Other relevant factors, which to some extent dictate the in vitro and in vivo behavior of the polymer, include the chemical composition, spatial distribution of the constituents, the molecular weight of the polymer, and the degree of crystallinity. The selection of polymer materials having varying resorption profiles would allow a multi-phase composition or implant to degrade in a step-wise manner, thus allowing for gradual tissue in-growth. Standard techniques used in the art such as varying molecular weight, copolymer ratio, and crystallinity can be used to further differentiate degradation properties of the polymers.

Granules have been used as a synthetic bone graft substitute, however the handling of loose granules with BMA/autograft has presented challenges during spinal fusion surgery, e.g., with respect to handling and containment of the granules at a site during a procedure. To address this challenge, the present inventor developed the present compositions e.g. in a putty form in which granules, powders and/or particulates may be held together by an inert, biocompatible, resorbable carrier.

Compositions

According to non-limiting example embodiments present compositions include a polymer component (such as Pluronic/poloxamer or PEG) and a soybean derived lipid/phospholipid component (such as "Phosal"). By way of non-limiting example, the polymer component of the carrier may include a poloxamer component (such as Pluronic F127 also known as Poloxamer 407, or other pluronic polymers) or a PEG polymer. The phospholipid component may be a Phosal component (such as Phosal 50 PG). The present carrier compositions, which include a soybean derived lipid mixed with a polymer having a low melting temperature (e.g., Pluronic F127 with a melt point of 60° C.) results in a unique carrier, which may be used as a carrier to deliver e.g., granules, powder and/or particulates. Thus, according to non-limiting example embodiments, the present compositions may further include one or more of granules, powder and particulates.

Granules: may include for example, MicroFuse granules or granules/beads made of e.g., PLGA or PLA or PCL as discussed further below. Powders may include for example, DBM (demineralized bone matrix) powder, or calcium phosphate powder. Particulates may include for example, ceramic/β-TCP particles such as Vitoss granules or MasterGraft.

According to non-limiting example embodiments, granules may include one or more of various grades of polymers, including but not limited to PLA, PLGA, PCL, etc. According to example embodiments, the granules may be biodegradable. Polymer granules may be useful for applications such as drug delivery, or delivery of growth factors. According to example embodiments, the polymer granules include at least two different types of granules having at least two different compositions. For example, the polymer granules may include granules having two or more different degradation rates. By way of non-limiting example embodiments, the at least two different types of granules may include for example, two or more types of PLGA and/or PLA microspheres. By way of further example, the at least two types of granules include 82:18 poly(L-lactide-co-glydolide) and 85:15 poly(D,L lactide-co-glycolide). It would be apparent to those skilled in the art that the granules may be various grades, including 82:18 PLGA, 85:15 PLGA, 70:30 PLDLA, etc.

According to non-limiting example embodiments, the polymer granules may be present in approximately equal amounts. For example, 82:18 poly(L-lactide-co-glydolide) and 85:15 poly(D,L lactide-co-glycolide) may be present in about a 50:50 mix. According to other embodiments, the polymers may be formed into microspheres and then combined in a range of about 95:5 to 5:95 depending on the desired resorption profile. In example embodiments, the ratio may be about 80:20-20:80 or 40:60-60:40 or 45:55-55:45 of the polymers or any range there-between depending e.g. on a desired resorption profile.

In exemplary embodiments, various forms of the same polymer, poly(lactide-co-glycolide), may be used to give particles with varying degradation profiles. The copolymer 82:18 poly(L-lactide-co-glycolide) has been shown to have a degradation time of 6-9 months while 85:15 poly(D,L lactide-co-glycolide) degrades in 2-3 months.

One could make the granules out of microspheres derived from these PLA/PLGA type polymers. One could also make granules from spheres out of two different types of polymers (e.g., 2 PLGAs, 1 PLA-1PLGA, 2 PLAs).

As discussed above, granules may include e.g., microspheres, beads, or other particles of similar or different shapes and sizes. The granules may be non-bonded, loose granules. According to non-limiting examples, the granules may include two or more types of PLGA of a granule size of about 600-850 micron. But the spheres/granules may be made out of any PLA/PLGA polymers in whatever size is desired. By way of non-limiting example, spheres may be made that are less than 125 microns, 125-250 microns, 250-500 microns, 600-850 microns, 850 microns and above, or any desirable size or range of sizes.

To form granules, after the spheres, beads, or other shaped particles are obtained, they may be thermally sintered or bonded e.g. by heating to obtain granules.

Granules herein may be for example, MicroFuse® Granules, which are a highly engineered bone void filler specifically designed with porosity and strength to provide an advantageous environment for regenerating bone. As indicated above, other granules, powders and/or particulates may be used in conjunction with the present phospholipid-based carriers either as part of the carrier or administered along therewith. By way of non-limiting example, granules, powders and particulates that may be used in accordance herewith may include one or more of the following:

a) Ceramic beads/particulates/granules, such as Vitoss granules (made of β-TCP),
b) Calcium Phosphate particles,
c) Hydroxyapatite particles,
d) Silicated hydroxyapatite particles,
e) Bioactive Glass particles,
f) Cancellous Chips (allograft bone)
g) Cortical bone chips (allograft bone), and/or
h) Demineralized Bone Matrix (DBM) chips or powder, As indicated above, the present compositions (which may be combined with the granules, powder and/or particulates) include at least one polymer component such as a poloxamer (pluronic) or PEG component, and at least one phospholipid component.

The polymer component may include for example, one or more poloxamers, such as Pluronic F127 or Poloxamer 407 or other polymers in the family of poloxamers/pluronics, which includes, but is not limited to Pluronic 10R5, Pluronic 17R2, Pluronic 17R4, Pluronic 25R2, Pluronic 25R4, Pluronic 31R1, Pluronic F 108 Cast Solid Surfacta, Pluronic F 108 NF, Pluronic F 108 Pastille, Pluronic F 108 Prill, Pluronic F 108 NF Prill Poloxamer 338, Pluronic F 127, Pluronic F 127 Prill, Pluronic F 127 NF, Pluronic F 127 NF 500 BHT Prill, Pluronic F 127 NF Prill Poloxamer 407, Pluronic F 38, Pluronic F 38 Pastille, Pluronic F 68, Pluronic F 68 Pastille, Pluronic F 68 LF Pastille, Pluronic F 68 NF, Pluronic F 68 NF Prill Poloxamer 188, Pluronic F68 Prill, Pluronic F 77, Pluronic F 77 Micropastille, Pluronic F 87, Pluronic F 87 NF, Pluronic F 87 NF Prill Poloxamer 237, Pluronic F 87 Prill, Pluronic F 88, Pluronic F 88 Pastille, Pluronic F 88 Prill, Pluronic F 98, Pluronic F 98 Prill, Pluronic L 10, Pluronic L 101, Pluronic L 121, Pluronic L 31, Pluronic L 35, Pluronic L 43, Pluronic L 44, Pluronic L 61, Pluronic L 62, Pluronic L 62 LF, Pluronic L 62D, Pluronic L 64, Pluronic L 81, Pluronic L 92, Pluronic L 44 NF INH surfactant Poloxamer 124, Pluronic N 3, Pluronic P 103, Pluronic P 104, Pluronic P 105, Pluronic P 123 surfactant, Pluronic P 65, Pluronic P 84, and Pluronic P 85. Pluronic F127 or Poloxamer 407 is a hydrophilic non-ionic surfactant of the more general class of copolymers known as poloxamers. Poloxamer 407 is a triblock copolymer consisting of a central hydrophobic block of polypropylene glycol flanked by two hydrophilic blocks of polyethylene glycol. The approximate lengths of the two PEG blocks is 101 repeat units while the approximate length of the propylene glycol block is 56 repeat units. The particular compound is also known by the BASF trade name Pluronic F127. As used herein, the term Pluronic F127 is intended to refer to all poloxamer 407 compounds whether made by BASF or any other maker.

As indicated above, the polymer component may comprise a Polyethylene Glycol (PEG) component, such as PEG of various grades PEG 1000, PEG 1500, PEG 2000, PEG 4000, PEG 8000, PEG 10000, and/or PEG 20000.

The phospholipid, such as Phosal 50 PG is a soybean derived component, and is a standardized phosphatidyl-choline concentrate with at least 50% PC and propylene glycol. Phosal 50 PG is just one member out of a family of Phosal series that may be used in accordance with the present invention, which includes other lipids such as Phosal 53 MCT, Phosal 75 SA, Phosal 25 PG, Phosal 35 SB, Phosal 50 SA, etc.

Certain phospholipids may not be suitable for the present compositions. For example, phospholipons may not be suitable, as they are solid.

According to example embodiments, the phospholipids of the present composition may be pharmaceutical grade.

The present carrier compositions may include for example about 35%-70% by weight of the polymer component (such as Pluronic F127) and about 65%-30% by weight of the phospholipid component (such as Phosal 50PG).

According to example embodiments, the present carriers may include for example about 59%-69% or about 64% by weight of the polymer component and about 31%-41% or about 36% by weight of the phospholipid component. These amounts may be particularly advantageous for example if granules are to be added to the carriers in forming the present compositions. The weight percents of polymer and phospholipid components would be different of course in an overall composition that further includes additional components such as granules. In this case, for example, the present composition may include for example about 33%-43% by weight of granules, about 35%-45% by weight of polymer component (such as Pluronic F127) and about 18%-27% by weight of phospholipic component (such as Phosal 50 PG). In particular, the composition may include about 38% by weight of biodegradable polymer granules, about 40% by weight of the Pluronic F 127, and about 22% by weight of the Phosal 50 PG.

According to example embodiments, the present carriers may include for example about 45%-50% by weight of the polymer component (such as Pluronic F127) and about 50%-55% by weight of the phospholipid component (such as Phosal 50PG). These amounts may be particularly advantageous for example if particulates or powder, such as ceramic particles (Vitoss or Mastergraft), bioactive glass, etc., are to be added to the carriers in forming the present compositions.

Thus, non-limiting example compositions that include a polymer component, phospholipid component, and at least one third component, may include the following the components (by weight %):

| When you use ... | MicroFuse Granules | Ceramic Particles | Bioactive Glass | DBM Powder |
|---|---|---|---|---|
| 3rd component | 33-43% | 45-55% | 40-50% | 40-50% |
| Polymer (e.g., Pluronic F127) | 35-45% | 22-32% | 22-32% | 22-32% |
| Phospholipid (e.g., Phosal 50PG) | 17-27% | 17-27% | 22-32% | 22-32% |

Thus, the final compositions may include for example about 22%-45% of the polymer component (e.g., Pluronic F127), about 17-32% of the phospholipid component (e.g., Phosal 50 PG), and about 33-55% of a third component (such as granules, powder, particles, etc).

According to non-limiting example embodiments, the present compositions may be in the form of a putty. According to non-limiting embodiments, the carrier may be soft, moldable and dough-like, or may have more or a paste like consistency before being combined or mixed with granules, powder or particulates. Such carrier may become more putty-like when combined with e.g., granules, powder and/or particulates. For example, a carrier composition that includes about 64% Pluronic F127 and about 36% Phosal 50PG would give a dough-like carrier that results in a putty-like formulation when mixed with MicroFuse Granules. A carrier composition that includes about 45-50% Pluronic F127 and about 50-55% Phosal 50PG would give a carrier with more of a paste like consistency. This is good for powdery or particulate materials.

Advantageous features of the present compositions may include one or more of the following: the phospholipid carrier will allow better handling of the granules at an implantation site in a mammal; the phospholipid carrier resorbs quickly in the body (e.g., in less than 5 days, or in less than 3 days, i.e., 72 hours) and will leave the granules behind for bone regeneration (the granules having one or more slower degradation rates of e.g., 2-3 months and/or 6-9 months), along with any other optional graft material and/or active ingredient; and the carrier is also osteopromotive, or in other words supports bone regeneration.

According to non-limiting example embodiments, the present compositions may further include one or more graft materials and/or one or more active ingredients. The one or more graft materials may include for example, synthetic BGS (Bone Graft Substitute). The graft materials may also include for example, bone, autogenous graft, blood, BMPs, growth factors, and/or ceramic particles. By way of example, the present compositions may include one or more of the following:

a) Ceramic beads/particulates/granules such as Vitoss granules (made of β-TCP),
b) Calcium Phosphate particles,
c) Hydroxyapatite particles such as MasterGraft,
d) Silicated hydroxyapatite particles,
e) Bioactive Glass particles,
f) Cancellous Chips (allograft bone),
g) Cortical bone chips (allograft bone),
h) Demineralized Bone Matrix chips or powder,
i) Growth factors such as BMP2, BMP7, and/or
j) Pain medication According to a non-limiting embodiment, the present invention has resulted in the development of e.g., MicroFuse® Putty which includes the MicroFuse® Granules.

Having the granules in a phospholipid based carrier would facilitate better handling containment of the granules at the site during a procedure. The superior handling of the product as a result of the addition of the carrier to the granules has been verified by numerous handling evaluations.

The superior handling of the present compositions, such as MicroFuse Putty, as a result of the addition of the phospholipid carrier has enabled the following:

1) Superior handling (soft, moldable and dough like) with a certain stickiness and tackiness to it;
2) Ability to mix additional graft materials such as bone/ autogenous graft/blood/BMA/ceramic particles without affecting the handling of the product;
3) Use of the product in posterolateral spinal fusion, as packing inside interbody cages and as a bone void filler (during surgery in bone grafting) in extremities, long bones, and CMF pelvis; and
4) Ability to use the composition for delivering BMPs/other growth factors or for drug delivery. This composition may also help in the containment/confinement of growth factors like BMP2 within an interbody cage which has a significant clinical benefit.

The present compositions may be administered to a mammal such as a human for various uses or applications. For example, the compositions may be administered as a bone graft substitute in the spine, extremities and/or pelvis. For bone grafting, the compositions may be used as bone void filler. The handling characteristics of example compositions have enabled it to be used e.g., in posterolateral spinal fusion, packing inside interbody cages, and as a bone void filler in extremities/long bones and pelvis devices, and CMF (Craniomaxillofacial) devices. The compositions may be used for drug delivery or for delivery of growth factors (such as PDGF, BMP, etc.). The carriers may also be used as a hemostatic agent (stops blood flow).

Implants

Other example embodiments include for example, one or more implant devices that may include a device for implantation into a mammal, such as a human, and the present composition on or in the device. The composition may additionally include any component that may be desirable for implantation or delivery with the device, such as bone graft materials and/or active ingredients.

The present devices may be used for various purposes e.g., posterolateral spinal fusion devices or interbody cages or other devices being implanted to a mammal for any number of reasons. The present compositions may be coated on or included in an implant device. Thus, the present invention further encompasses such devices having one or more of the present compositions thereon or therein.

Method of Making Compositions and Preparing Compositions for Delivery

Non-limiting example embodiments herein include methods of making the present carrier compositions for implantation into a mammal. In the present methods of preparing compositions for delivery to a mammal, one may start out e.g., with granules (e.g., MicroFuse Granules), powder or particulates; or with a composition (e.g., MicroFuse Putty) that may contain one or more of granules, powder and particulates; and add blood or bone marrow aspirate (BMA) thereto. BMA is essentially blood except that it has more of the cells that are needed for bone regeneration.

By way of example of combining blood or BMA with granules, powder or particulates, FIG. 4 shows the addition of the BMA to MicroFuse Granules (FIG. 1) directly. Because the Granules are all porous they wick in the blood.

As indicated above, further examples include adding blood or BMA with a composition that includes polymer, phospholipid and at least one of granules, powder or particulates. The methods may include mixing the present compositions with at least one component selected from the group consisting of one or more graft materials and one or more active ingredients.

Thus, non-limiting example embodiments herein include methods of making the present compositions, which may include for example, preparing a mixture of polymer and phospholipid to make a carrier. The methods may further include mixing one or more granules, powders, particulates, graft materials and/or active ingredient with the carrier. By way of non-limiting example, an embodiment of the present composition may include mixing together polymer granules (e.g. MicroFuse® ST granules), pluronic F127 and Phosal 50 PG to make a MicroFuse putty composition. According to example embodiments, the carrier may be first prepared and one or more granules, powders and/or particulates or other ingredients mixed therewith. The ingredients may be mixed however in another order or simultaneously.

By way of example, the present methods may include providing a carrier composition (which includes the polymer and phospholipid components and optional additional components, such as MicroFuse granules) in a bowl and mixing blood or bone marrow aspirate (BMA) into the composition. By way of non-limiting example, the mixing may take place using a gloved hand. According to example embodiments, bone may also be added to the composition and mixing of the ingredients (MicroFuse putty, blood/marrow, and bone) can be performed using fingers (gloved hand). In these examples, because the pores of the granules are filled with the carrier material the granules in the putty don't wick in the BMA. The handling of these final formulations is excellent even in the presence of blood/BMA and bone (Carrier/Granules), (Carrier/Powder), (Carrier Particulates).

Other non-limiting example embodiments herein include methods of making the present compositions, which may include for example, mixing polymer granules (e.g. MicroFuse® ST granules) for example, in a syringe, with the phospholipid carrier that includes Pluronic F127 and Phosal 50 PG to make a putty composition.

Figure 1:
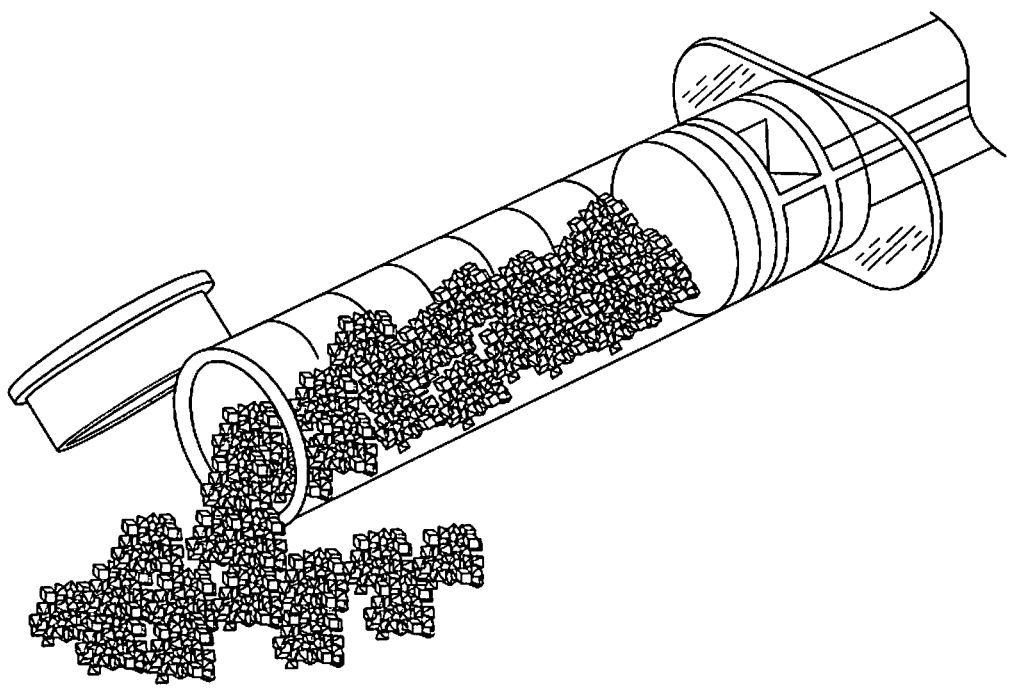
FIG. 1 depicts a syringe having therein synthetic bone graft substitute polymer granules by Globus Medical, Inc., under the trade name MicroFuse® Granules, which may be added e.g., to the present carrier compositions.
Figure 2:
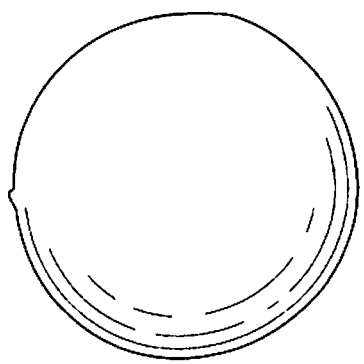
FIG. 2 depicts a non-limiting example of a phospholipid-based carrier of the present invention, which in the depicted embodiment includes Pluronic F127 and Phosal 50 PG. In the depicted embodiment, the carrier is a bioresorbable carrier in the form of a putty, which has been shaped into a ball. It should be understood, however, that the carrier can be shaped into any desirable shape.

For example, as shown in FIG. 3, biodegradable polymer granules, such as the MicroFuse® Granules depicted in FIG. 1, may be combined with a bioresorbable phospholipid-based carrier, which includes for example, Pluronic F127 and Phosal 50 PG, as depicted in FIG. 2, to form novel carrier compositions according to the present invention. Although in FIG. 3 the composition (entitled "MicroFuse Putty" in the figure) is within a syringe-like delivery device, it should be understood that the compositions may be administered in any number of ways to a subject, for example within or on an implant device that will be implanted into the mammal. Additionally, although FIG. 3 depicts the use of particular granules (i.e., MicroFuse granules), it is contemplated that other biodegradable polymer granules may be substituted therefore and formed into the present compositions in accordance with the present invention.

The present invention further encompasses methods of making compositions for implantation into a mammal, which include mixing at least one of the present compositions with at least one component selected from the group consisting of one or more graft materials and one or more active ingredients. The bone graft materials may include for exemplary graft material discussed herein or otherwise known to those skilled in the art, including, but not limited to bone, autogenous graft, blood, BMP, growth factors, and ceramic particles.

Further included are methods as depicted for example, in FIG. 7, which include heating a polymer to form a melted polymer, combining a phospholipid with the melted polymer, adding at least one addition component selected from granules, powder and particulates, and kneading the polymer, phospholipid and at least one additional component until a mixture of the polymer, phospholipid and at least one additional component hav a temperature of about 38-48° or about 43° C.

Methods of Treating Mammals

Also provided are methods of treating mammals, such as humans, by administering to a mammal at least one of the present compositions. Additional methods of treatment may include for veterinary applications. Those skilled in the art would be able to ascertain, which mammals may be treated by the various methods. According to non-limiting example embodiments the at least one additional component selected from the group consisting of one or more graft materials and one or more active ingredients may also be administered either as part of the composition, or in addition thereto. According to non-limiting example embodiments, the present compositions may be directly administered to a mammal or they may be administered either on or in an implant that is inserted into a mammal, e.g., during a surgical procedure. According to example embodiments the one or more graft materials and/or one or more active ingredients may be administered (e.g. included in the composition) in an effective amount for achieving an intended purpose of the graft materials and/or active ingredient in the mammal being treated. An effective amount may be determined by one skilled in the art such as a physician. Non-limiting examples of additional ingredients or active ingredients that may be administered in accordance with the present invention may include e.g., ingredients for drug delivery (e.g., with loaded microspheres), pain medication, and/or delivering growth factors (PDGF, BMP etc.)

According to non-limiting example embodiments, the present compositions may be administered to a mammal by themselves, or alternatively in or on an implant that is inserted into a mammal.

Such methods may further include administering one or more graft materials and/or one or more active ingredients, either as part of the present compositions or along therewith.

Kits

Other example embodiments are directed to kits that include the present compositions or one or more ingredients thereof, and may further include e.g., instructions for making and/or using the compositions; one or more implant devices into or onto which the composition may be incorporated; granules, powders or particles, tools or devices for mixing and/or storing the compositions; tools or devices for inserting the present compositions or implant devices into a mammal; one or more graft materials and/or active ingredients that may be provided with or carried by the present compositions; and/or any other components or devices that may be useful in making and/or using the present compositions or implant devices.

Kits provided herein may include for example, one or more polymers such as pluronic or PEG polymers, and one or more phospholipids, such as a Phosal. By way of example, kits may include Pluronic F127 and Phosal 50 PG, and optionally one or more of the additional ingredients discussed herein, such as granules, powders and/or particles. By way of example, kits provided herein may include Microfuse Granules; Pluronic F127, and Phosal 50 PG.

The following examples are provided to further illustrate various non-limiting embodiments and techniques encompassed by the present invention. It should be understood, however, that these examples are meant to be illustrative and do not limit the scope of the claims. As would be apparent to skilled artisans, many variations and modifications are intended to be encompassed within the spirit and scope of the present disclosure.

EXAMPLES

Example 1

Compositions according to the present invention may be prepared e.g., in any of the following different sizes (which are similarly sizes in which loose polymer granules may be available): 2.5 cc, 5 cc, 10 cc and 20 cc (e.g. in syringes). It should be understood that other size preparations may be made as well. The following table sets forth various non-limiting example embodiments of compositions in the indicated volumes:

MicroFuse Putty Composition by Weight

| Volume | Weight (gm) | MicroFuse ST Granules 38% (by weight) | Pluronic F127 40% (by weight) | Phosal 50PG 22% (by weight) |
| --- | --- | --- | --- | --- |
| 2.5 cc | 2.75 | 1.05 | 1.10 | 0.60 |
| 5 cc | 5.5 | 2.10 | 2.20 | 1.20 |
| 10 cc | 11 | 4.20 | 4.40 | 2.40 |

In each of the above formulations, polymer granules (i.e., MicroFuse® granules) are mixed with indicated amounts of Pluronic F127 and Phosal 50.

Example 2

In this example, a method for preparing a carrier composition according to the present embodiments is described.

FIG. 6 depicts example raw materials that may be used in example embodiments of the carrier composition of the present application. The method of making the present example carrier and the order of steps are as follows:

Step 1

The polymer is heated at 140° C. for 2 hrs to completely melt the polymer.

Step 2

After the polymer is melted, a phospholipid e.g., Phosal 50PG is added to the polymer (for example in a mixing bowl) and mixing is carried out e.g., on a Hamilton Beach Mixer. The temperature of the batch is measured using a temperature data logger with the thermocouple placed on the bowl on the outside. Initially, the mix appears golden yellow and is entirely a liquid. Over time, as the temperature of the batch falls down and the mix appears to have a cake mix like consistency. As this is progressively going on, the polymer (in this example, Pluronic F127) cools down below its melt point causing the mix to turn lemon yellow. This takes about 15-20 minutes depending on the size of the batch.

Step 3

When the temperature on the batch falls down to 39° C. (measured on the outside), Granules are added to the Carrier Mix and the mixing is continued for about 1 min. The temperature on the inside is going to be higher and hence the granules can only be added once the temperature set point of 39° C. has been attained.

Step 4

The consistency of the Granule/Carrier mix changes to a thick viscous state after approximately 1 minute of mixing. The whole batch is then scooped out and the kneading of the Granule/Carrier batch is carried out e.g., on the Electrolux Assistent Mixer until the temperature of the batch falls down to about 41° C.-45° C. or about 43° C. If the Granule/Carrier mix is not kneaded until it cools down, it changes to a solid waxy state. This is a very important phenomenon which was observed during development. The kneading of the granule/carrier mix resulted in a soft doughy putty whereas cooling of the batch without kneading resulted in a rigid waxy end product. This may be explained by the fact that the addition of the soybean oil (Phosal 50PG) probably results in the introduction of the lipid molecules within the amorphous polymer (Pluronic F127) network which prevents the melted polymer from reverting back to a rigid solid state.

Although the invention has been described in example embodiments, those skilled in the art will appreciate that various modifications may be made without departing from the spirit and scope of the invention, and such modifications are therefore included herein. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto.

What is claimed is:

1. A composition comprising about 22-70% by weight of at least one polymer component and about 17-65% by weight of at least one phospholipid component,
the composition further comprises one or more graft materials, wherein the one or more graft materials comprise synthetic BGS (bone graft substitute).

2. The composition of claim 1, wherein the polymer component comprises at least one poloxamer or Polyethylene Glycol polymer and the phospholipid component comprises at least one phosopholipid component.

3. The composition of claim 1, wherein the composition further comprises at least one additional component selected from the group consisting of granules, powders and particulates.

4. The composition of claim 1, wherein the composition further comprises granules comprising at least two different types of granules having different degradation rates.

5. The composition of claim 4, wherein said at least two different types of granules comprise 82:18 poly (L-lactide-co-glydolide) and 85:15 poly {D,L lactide-co-glycolide).

6. The composition of claim 4, wherein said at least two different types of granules are present in approximately equal amounts.

7. The composition of claim 1, wherein the composition comprises about 35-70% by weight of the polymer component, and about 30-65% by weight of the phospholipid component.

8. The composition of claim 1, wherein the composition comprises about 22-45% by weight of the polymer component, about 17-32% by weight of the phospholipid component; and about 33-55% by weight of a third component selected from the group consisting of granules, powder and particulates.

9. The composition of claim 1, wherein the composition is in the form of a putty.

10. The composition of claim 1, further comprising at least one component selected from the group consisting of one or more graft materials and one or more active ingredients.

11. An implant comprising a device for placement in a mammal, and the composition of claim 1 thereon or therein.

12. The implant of claim 11, wherein said device comprises a device selected from the group consisting of posterolateral spinal fusion devices, interbody cage packing, bone void filler in extremities/long bones and pelvis devices, and CMF (Craniomaxillofacial) devices.

13. A kit comprising the composition of claim 1, and at least one additional component selected from the group consisting of instructions for using the composition, a device for implantation into a mammal; one or more granules, powders or particulates; an active ingredient; tools and/or devices for making and/or storing the composition; a graft material; and tools or delivery devices for administering the composition or implant devices to a mammal.

* * * * *